US010531666B2

(12) United States Patent
Jaronski et al.

(10) Patent No.: US 10,531,666 B2
(45) Date of Patent: Jan. 14, 2020

(54) COMPOSITIONS AND METHODS TO REDUCE THE POPULATION OF WHEAT-STEM SAWFLY AND HESSIAN FLY

(71) Applicants: The United States of America, as Represented by the Secretary of Agriculture, Washington, DC (US); Montana State University, Bozeman, MT (US)

(72) Inventors: Stefan Jaronski, Sidney, MT (US); Gadi Reddy, Conrad, MT (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/972,399

(22) Filed: May 7, 2018

(65) Prior Publication Data

US 2018/0325120 A1  Nov. 15, 2018

Related U.S. Application Data

(60) Provisional application No. 62/504,100, filed on May 10, 2017.

(51) Int. Cl.
*A01N 63/04* (2006.01)
*A01N 65/00* (2009.01)

(52) U.S. Cl.
CPC ............. *A01N 63/04* (2013.01); *A01N 65/00* (2013.01)

(58) Field of Classification Search
None
See application file for complete search history.

(56) References Cited

U.S. PATENT DOCUMENTS 8,709,399 B2   4/2014  Vidal et al.

OTHER PUBLICATIONS

Kaaya et al . J Invertebr Pathol. 66(3):237-41 (Year: 1995).*
Akutse, K.S. et al., "Endophytic colonization of Vicia faba and Phaseolus vulgaris (Fabaceae) by fungal pathogens and their effects on the lifehistory parameters of Liriomyza huidobrensis (Diptera: Agromyzidae)," Fungal Ecology, (2013), 6:293-301.
Batta, Yacoub A. et al.,"Efficacy of endophytic and applied Metarhizium anisopliae (Metch.) Sorokin (Ascomycota: Hypocreales) against larvae of Plutella xylostella L. (Yponomeutidae: Lepidoptera) infesting Brassica napus plants," Crop Protection, (2013), 44:128-134.
Beres, B.L. et al., "Host plant interactions between wheat germplasm source and wheat stem sawfly Cephus cinctus Norton (Hymenoptera: Cephidae) I. Commercial cultivars," Can. J. Plant Sci., (2013), 93:607-617.
Bing, Lori Anderson et al., "Endophytic beauveria bassiana (balsamo) vuillemin in corn: The influence of the plant growth stage and ostrinia nubilalis (hübner)," Biocontrol Science and Technology, (1992), 2:1, 39-47.
Gomez-Vidal, Sonia et al., "Research Article: Proteomic analysis of date palm (Phoenix dactylifera L.) responses to endophytic colonization by entomopathogenic fungi," Electrophoresis, (2009), 30:2996-3005.
Guesmi-Jouini, J. et al., "Establishment of fungal entomopathogens Beauveria bassiana and Bionectria ochroleuca (Ascomycota: Hypocreales) as endophytes on artichoke Cynara scolymus," Journal of Invertebrate Pathology, (2014), 119:1-4.
Gurulingappa, Pampapathy et al., "Colonization of crop plants by fungal entomopathogens and their effects on two insect pests when in planta," Biological Control, (2010), 55:34-41.
Jaronski, Stefan et al., "First Isolation of Beauveria and Metarhizium from a wheat stem borer, Cephus cinctus (Hymenoptera: Cephidae) in North America," SIP 2015 Abstract.
Khan, Abdul Latif et al., "Pure culture of Metarhizium anisopliae LHL07 reprograms soybean to higher growth and mitigates salt stress," World J. Microbiol Biotechnol, (2012), 28:1483-1494.
Knodel, Janet J. et al., "Pest Management of Wheat Stem Maggot (Diptera: Chloropidae) and Wheat Stem Sawfly (Hymenoptera: Cephidae) Using Insecticides in Spring Wheat Author(s): Janet J. Knodel, Patrick B. Beauzay, Eric D. Eriksmoen," Journal of Agricultural and Urban Entomology, (2009), 26(4):183-197.
Montana Wheat and Barley Committee Meeting Feb. 26, 2015.
Ownley, Bonnie H. et al., "Beauveria bassiana: Endophytic colonization and plant disease control," Journal of Invertebrate Pathology, (2008), 98:267-270.
Posada, Francisco et al., "Inoculation of coffee plants with the fungal entomopathogen Beauveria bassiana (Ascomycota: Hypocreales)," Mycological Research, (2007), 111(6): 745-757.
Quesada-Moraga, B.B. et al., "Endophytic colonisation of opium poppy, Papaver somniferum, by an entomopathogenic Beauveria bassiana strain," Mycopathologia, (2006), 161:323-329.
Reay, S.D. et al., "Isolation and characterization of endophytic Beauveria spp. (Ascomycota: Hypocreales) from Pinus radiata in New Zealand forests," Biological Control, (2010), 54:52-60.
Tefera, Tadele et al., "Effect of inoculation method and plant growth medium on endophytic colonization of sorghum by the entomopathogenic fungus Beauveria bassiana," BioControl, (2009), 54:563-669.
Jean, Renee et al., "Unraveling the secrets of the sawfly," Williston Herald Jul. 6, 2015 article.

* cited by examiner

*Primary Examiner* — Padmavathi Baskar
(74) *Attorney, Agent, or Firm* — John D. Fado; Maria Restrepo-Hartwig

(57) ABSTRACT

Novel strains of *Beauveria pseudobassiana, B. amorpha, B. bassiana, Metarhizium pemphigi,* and *M. anisopliae* have been isolated from wheat stem sawfly and demonstrated to endophytically colonize wheat and kill wheat stem sawfly and Hessian fly larvae diapausing in the stems of the wheat. Biocontrol compositions containing at least one of these fungal strains in an effective amount to kill wheat stem sawfly and Hessian fly larvae are generated. One can apply at least of these fungal strains or a biocontrol composition containing at least one of these fungal strains to a grain crop field or land where wheat stem sawfly and Hessian fly larvae live in order to kill the larvae and to reduce the population of the diapausing wheat stem sawfly and Hessian fly larvae.

9 Claims, 7 Drawing Sheets

FIG. 6

Figure 1:
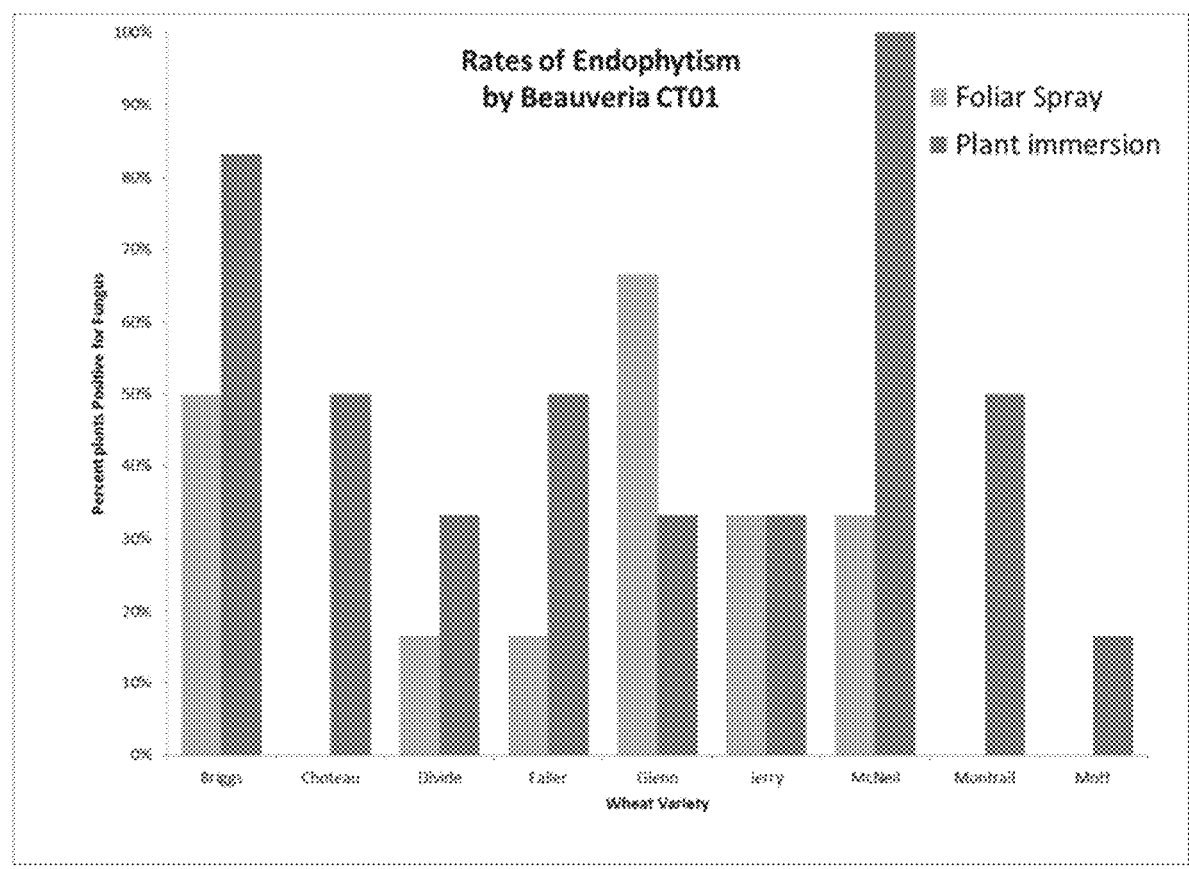

COMPOSITIONS AND METHODS TO REDUCE THE POPULATION OF WHEAT-STEM SAWFLY AND HESSIAN FLY

CROSS REFERENCE TO RELATED APPLICATIONS

This patent application claims priority to U.S. Patent Application 62/504,100 filed on May 10, 2017, contents of which are expressly incorporated by reference herein.

BACKGROUND OF THE INVENTION

Field of the Invention

This invention relates to methods to reduce the population of active or diapausing wheat stem sawfly larvae (*Cephus cinctus*) and active or diapausing Hessian fly larvae (*Mayetiola destructor*) by applying an effective amount of one or more fungal strains that kill the larvae to an area of land or to plants. This invention also relates to *Beauveria pseudobassiana*, *B. amorpha*, *B. bassiana*, *Metarhizium pemphigi*, and *M. anisopliae* strains, isolated from wheat stem sawfly, which are endophytic in wheat, and can infect and kill wheat stem sawfly and Hessian fly larvae, and biocontrol compositions containing one or more of these fungal strains. The invention also relates to kits used for the application of one or more of these fungal strains and/or biocontrol compositions containing one or more of these fungal strains.

Description of Related Art

The wheat stem sawfly, a grass-mining cephid attacking wild grasses and small grains, is the most important pest of wheat in the plains region of the northern U.S. and southern Canada. See Morrill and Kushnak, *J. Agri. Urban Entomology* 16(2): 123-128 (1999) and Shanower and Waters, *J. Entom. Sci.* 41(1): 40-48 (2006). Adults emerge in the spring at about the time of stem elongation in both winter and spring wheat, and insert their eggs into the stem of the wheat plant. The larvae hatch within a few days and feed on the internal parenchyma, living entirely within the wheat stem. There is some yield loss during this early development, but major damage occurs in late July when the larvae descend to the base of the plants and create hibernacula for overwintering. In the process the larva notches the wheat stem above its hibernaculum, greatly weakening the stem. This damage causes the mature wheat to lodge with wind or hail, and renders the grains generally unharvestable. Yield losses occur because of larval tunneling and stem lodging. Heavy infestations, greater than 80%, can be common. Wahl, et al., *J. Kansas Entom. Soc.* 80(1):43-50 (2007). Annual losses are estimated at more than $100 million just in Montana. Except for the adult stage, entire development of *C. cinctus* takes place inside the plant. The larva overwinters in this hibernaculum, just above the soil level to emerge the following spring.

The Hessian fly is another serious stem-dwelling pest of wheat, with an ecology similar to that of the sawfly, and susceptible to lethal infection by *Beauveria* and *Metarhizium*. Hessian fly is frequently considered the most important pest of winter wheat outside the Northern Plains (where wheat stem sawfly reigns), and also attacks barley and rye. It is particularly important in Midwest wheat, but is a severe pest throughout many wheat-growing regions of the world (Wellso & Wetzel 1987). This insect has two generations a year, a fall brood that overwinters in winter wheat as a pupal 'flaxseed stage,' with adult emergence in March-April. This brood attacks spring wheat as the main annual, "spring brood." The spring brood in turn matures to the pupal stage, but remains dormant during the remainder of summer, to become the "fall brood." With each brood, eggs are laid in the grooves of younger leaves. After 3-10 days larvae hatch out and move down the plant between leaf sheath and stem to just above the wheat plant's crown. Larvae feed on plant sap 8-30 days, then pupate. The larval feeding on the stem beneath the leaf sheath, combined with high infestation levels can stunt or kill plants; prevent spike development; reduce grain fill; and weaken stems resulting in lodging.

In North America, current wheat stem sawfly management practices are generally limited to the use of resistant solid-stemmed cultivars, which are partially effective but have significant disincentives for producer adoption because of reduced yields, poor protein content, and variable solid-stem trait expression depending on environmental conditions (Beres, et al., *Can. J. Plant Sci.* 93(4): 607-617 (2013)). Pesticides are either ineffective or cost more than the economic yield return (Knodel, et al., *J. Agri. Urban Entom.* 26(4):183-197 (2009)). Ironically, the spread of no-till agriculture benefits the insect and has increased its impact. The development of alternative control approaches, such as biological control, is needed to expand options for controlling this important pest (i.e., reducing the population of the insect by killing the larvae).

No remedial measures are available for Hessian fly management. The main management tools are development of resistant cultivars, incorporating one or more identified resistance genes, in response to the insects' developed resistance to existing cultivars, in a continuing cycle of co-evolution. Crop rotation in infested fields is recommended but often difficult in the face of wheat-wheat rotations.

*Beauveria* spp. have been reported to endophytically colonize plants either via naturally occurring colonization or via deliberate inoculation. Endophytic colonization of *B. bassiana* has been reported in cocoa (Posada, et al., *Revista U.D.C.A. Actualidad & Divulgación Científica*, 13(2):71-78 (2010)), opium poppy (Quesada-Moraga, et al., *Mycopathologia* 161(5):323-329 (2006)), date palm (Gomez-Vidal, et al., *Electrophoresis* 30(17):2996-3005 (2006); Arab and El-Deeb, Sci. *J. King Faisal Univ* 13(2):91-101 (2012)), coffee (Posada, et al., *Mycological Research*, 111(6):748-757 (2007)), cotton and pumpkin (Gurulingappa, et al., *Bio. Control* 55(1):34-41 (2010)), tomato (Ownley, et al., *J. Invert. Path.* 98(3):267-270 (2008)), grapes (Rondot, et al., *Julius-Kühn-Archiv.* 438:386 (2012)), rape (Lohse, et al., Bio. Control, 88(1):26-36 (2015)); banana (Akello, et al., *Entom. Experian. et Applicata*, 129(2):157-165 (2008)), sorghum (Tefera and Vidal, *BioControl*, 54(5):663-669 (2009)), pine (Reay, et al., *Bio. Control* 54(1):52-60 (2010)), artichoke (Guesmi-Jouni, et al., *J. Invertebr. Pathol.* 119:1-4 (2014), and in broad bean (Akutse, et al., *Fungal Ecology* 6(4):293-301 (2013)), and has been attributed to providing a protective presence against certain pathogens in some cases. There is one report of an endophytic *Metarhizium*, identified as *M. anisopliae*, in rape (*Brassica napus*) (Batta, Y. A., *Crop Protection* 44:128-134 (2013)). Phytohormone effects from induced *Metarhizium* root endophytism in soybean, mitigating salt stress, has been reported (Khan et al., *World J. Microbiol. Biotechnol.* 28:483-1494 (2012).

Deliberate endophytism establishment by *Beauveria* has been accomplished by root dips into spore suspensions, treating seeds, and spraying plants. See, e.g., Tefera and Vidal (2009); and Landa, et al., *J. Invert. Path.*, 114(2):128-

138 (2013). Leaf miner survival and damage was observed to be significantly reduced in bean plants with endophytic *Beauveria* (Akutse, et al. (2013)), indicating the potential for biocontrol in this particular system.

A need exists for methods for the reducing the population of wheat stem sawfly and related stem borers using a non-chemical approach. To meet this need, two strains of *B. pseudobassiana* (CT01, CT10), one strain of *B. amorpha* (CT14), three strains of *B. bassiana* (15CT13, 15CT44, and 16WS07), two strains of *M. pemphigi* (CT19 and WS64), and one strain of *M. anisopliae* (16WS10) have been isolated from wheat stem sawfly larvae, and determined to be endophytic in grain crops and cause fatal infections in wheat stem sawfly larvae (*C. cinctus*) and Hessian fly larvae (*M. destructor*).

BRIEF SUMMARY OF THE INVENTION

It is an object of this invention to have a biocontrol composition that contains an agriculturally acceptable carrier and an effective amount of at least one endophytic fungal strain that kills wheat stem sawfly larvae and Hessian fly larvae. It is a further object the invention that the endophytic fungus can be *Beauveria pseudobassiana* strain CT01 (NRRL Access. No. 67405), *B. pseudobassiana* strain CT10 (NRRL Access. No. 67401), *B. amorpha* strain CT14 (NRRL Access. No. 67402), *Metarhizium* pemphigi strain CT19 (NRRL Access. No. 67405), *M. pemphigi* strain WS64 (NRRL Access. No. 67404), *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), and *M. anisopliae* strain 16WS10 (NRRL Access. No. 67612) or a combination thereof. It is another object of this invention that the effective amount of the endophytic fungus ranges between approximately $10^4$ to approximately $10^{12}$ spores per unit dose (e.g., ml liquid, gram powder, area of land, seed, etc.) or between approximately $10^4$ to approximately $10^{11}$ CFU vegetative mycelium per dose unit. The agriculturally acceptable carrier can be a polymer, a vegetable oil, a vegetable wax, a paraffinic oil, a paraffinic wax, an emulsion of oil and water, an aqueous solution containing a polymer, agar, gelatin, and a plant seed (or, more specifically, a grain crop seed). It is another object of this invention that the carrier is a lipophilic substance that assists the spores or vegetative mycelium in adhering to the plant. It is another object that the grain crop is wheat, triticale, spelt, rye, and/or barley.

It is an object of this invention to have a method of reducing the population of wheat stem sawfly larvae and Hessian fly larvae in an area of land by applying to the land an effective amount of the above described biocontrol composition to kill wheat stem sawfly larvae and Hessian fly larvae. It is another object of this invention that the applying step involves broadcasting on the land or planting seeds coated with approximately $10^4$ to approximately $10^{12}$ spores of at least one of the fungal strains, *B. pseudobassiana* strain CT01 (NRRL Access. No. 67405), *B. pseudobassiana* strain CT10 (NRRL Access. No. 67401), *B. amorpha* strain CT14 (NRRL Access. No. 67402), *M. pemphigi* strain CT19 (NRRL Access. No. 67403), *M. pemphigi* strain WS64 (NRRL Access. No. 67404), *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), or *M. anisopliae* strain 16WS10 (NRRL Access. No. 67612), or a combination thereof. It is a further object of the invention that the applying step involves broadcasting onto the land or planting seeds coated with between approximately $10^4$ to approximately $10^{11}$ CFU of vegetative mycelium of at least one of the fungal strains, *B. pseudobassiana* strain CT01 (NRRL Access. No. 67405), *B. pseudobassiana* strain CT10 (NRRL Access. No. 67401), *B. amorpha* strain CT14 (NRRL Access. No. 67402), *M. pemphigi* strain CT19 (NRRL Access. No. 67403), *M. pemphigi* strain WS64 (NRRL Access. No. 67404), *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), or *M. anisopliae* strain 16WS10 (NRRL Access. No. 67612), or a combination thereof. It is also another object of this invention that the applying step involves spraying the biocontrol composition onto grain crop plants or parts of the grain crop plants on the land, where the biocontrol composition contains spores or vegetative mycelium of at least one of these strains of fungi. It is a further object of the invention that the agriculturally acceptable carrier can be a polymer, a vegetable oil, a vegetable wax, a paraffinic oil, a paraffinic wax, an emulsion of oil and water, an aqueous solution containing a polymer, agar, gelatin, or any lipophilic substance that assists the spores or vegetative mycelium in adhering to the plant or part thereof, such as leaves, seeds, stems, branches, roots, and a combination thereof. It is a further object of this invention that the grain crop plant is wheat, triticale, spelt, rye, and/or barley.

It is an object of this invention to have a method of killing wheat stem sawfly larvae or Hessian fly larvae in a grain crop field by applying the biocontrol composition described above in an amount effective so that the fungus or fungi endophytically colonize grain crop plants in said grain crop field and kill the wheat stem sawfly larvae or Hessian fly larvae. It is another object of this invention that the applying step involves broadcasting or planting grain crop seeds coated with between approximately $10^4$ to approximately $10^{12}$ spore of at least one endophytic fungi onto the grain crop field. It is yet another object of this invention that the applying step involves spraying onto the grain crop plants or parts thereof a liquid containing between approximately $10^4$ to approximately $10^{11}$ CFU of vegetative mycelium of at least one of the endophytic fungi per liter liquid. It is another object of this invention that the applying step involves spraying a liquid containing between approximately $10^4$ to approximately $10^{12}$ spores of at least one endophytic fungi per liter of liquid onto the land or the grain crop plant or parts thereof in the grain crop field. It is a further object of the invention that the agriculturally acceptable carrier can be a polymer, a vegetable oil, a vegetable wax, a paraffinic oil, a paraffinic wax, an emulsion of oil and water, an aqueous solution containing a polymer, agar, gelatin, or any lipophilic substance that assists the spores or vegetative mycelium in adhering to the plant or part thereof. It is another object that the grain crop is wheat, triticale, spelt, rye, and/or barley.

It is another object of this invention to have a kit containing a first container, optionally a second container, and instructions. The first container has spores or vegetative mycelium of at least one endophytic fungus that kills wheat stem sawfly larvae or Hessian fly larvae such as *B. pseudobassiana* strain CT01 (NRRL Access. No. 67405), *B. pseudobassiana* strain CT10 (NRRL Access. No. 67401), *B. amorpha* strain CT14 (NRRL Access. No. 67402), *M. pemphigi* strain CT19 (NRRL Access. No. 67403), or *M. pemphigi* strain WS64 (NRRL Access. No. 67404) *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), or *M. anisopliae* strain 16WS10 (NRRL Access. No. 67612), or a combination thereof. The instructions describe how to apply the at least one endophytic fungus to land or a plant. The optionally second container has an agriculturally acceptable carrier. The agriculturally acceptable carrier can be a polymer, a vegetable oil, a vegetable wax, a paraffinic oil, a paraffinic wax, an emulsion of oil and water, an aqueous solution containing a polymer, agar, gelatin, or any lipophilic substance that assists the spores or vegetative mycelium in adhering to the plant or part thereof.

BRIEF DESCRIPTION OF THE SEVERAL VIEWS OF THE DRAWINGS

FIG. 1 shows the colonization rates (as a percentage of treated plants) of the indicated wheat varieties by *B. pseudobassiana* strain CT01 (NRRL Access. No. 67405) following foliar spray of $1\times10^8$ conidia/ml or plant immersion into a conidia-containing suspension of the same concentration.

FIG. 2 shows the colonization rates (as a percentage of treated plants) of the indicated wheat varieties by *B. pseudobassiana* strain CT10 (NRRL Access. No. 67401) following foliar spray of $1\times10^8$ conidia/ml or plant immersion into a conidia-containing suspension of the same concentration.

FIG. 3 shows the colonization rates (as a percentage of treated plants) of the indicated wheat varieties by *B. amorpha* strain CT14 (NRRL Access. No. 67402) following foliar spray of $1\times10^8$ conidia/ml or plant immersion into a conidia-containing suspension of the same concentration.

FIG. 4 shows the colonization rates (as a percentage of treated plants) of the indicated wheat varieties by *M. pemphigi* strain CT19 (NRRL Access. No. 67403) following foliar spray of $1\times10^8$ conidia/ml or plant immersion into a conidia-containing suspension of the same concentration.

FIG. 5 shows the colonization rates (as a percentage of treated plants) of the indicated wheat varieties by *M. pemphigi* strain WS64 (NRRL Access. No. 67404) following foliar spray of $1\times10^8$ conidia/ml or plant immersion into a conidia-containing suspension of the same concentration.

FIG. 6 shows the colonization rates (as a percentage of treated plants) of wheat varieties Reeder and Vida by *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), and *M. anisopliae* strain 16WS10 (NRRL Access. No. 67612) following plant immersion into a suspension of $5\times10^7$ conidia/ml.

FIG. 7 shows a comparison of the colonization rates (as a percentage of treated plants) of two wheat varieties (Choteau or Mott) by commercially available fungi (*M. robertsii* DWR2009, *M. anisopliae* ESF 1, *M. brunneum* F52, and *B. bassiana* GHA) or by the fungi of this invention (*Beauveria pseudobassiana* strains CT01 (NRRL Access. No. 67405) and CT10 (NRRL Access. No. 67401), *B. amorpha* strain CT14 (NRRL Access. No. 67402), and *Metarhizium* pemphigi strains CT19 (NRRL Access. No. 67403) and WS64 (NRRL Access. No. 67404)) after foliar application with oil-in-water emulsion containing conidia at a concentration of $1\times10^8$ conidia/ml.

DEPOSIT OF BIOLOGICAL MATERIAL UNDER TERMS OF BUDAPEST TREATY

The inventors deposited samples of the biological materials listed in Table 1 infra that are described and claimed herein, on the indicated date with the U.S.D.A., *Agricultural Research* Service, Patent Culture Collection located at the National Center for Agricultural Utilization Research, 1815 N. University Street, Peoria, Ill. 61604, in a manner affording permanence of the deposit and ready accessibility thereto by the public if a patent is granted. These deposits have been made under the terms of the Budapest Treaty on the International Recognition of the Deposit of Microorganisms for the Purposes of Patent Procedure and the regulations thereunder.

TABLE 1

| Genus species/strain designation | Deposit Date | NRRL Accession Number |
|---|---|---|
| *Beauveria pseudobassiana* strain CT01 | Mar. 10, 2017 | 67405 |
| *Beauveria pseudobassiana* strain CT10 | Mar. 10, 2017 | 67401 |
| *Beauveria amorpha* strain CT14 | Mar. 10, 2017 | 67402 |
| *Metarhizium pemphigi* strain CT19 | Mar. 10, 2017 | 67403 |
| *Metarhizium pemphigi* strain WS64 | Mar. 10, 2017 | 67404 |
| *Beauveria bassiana* strain 15CT13 | Apr. 12, 2018 | 67609 |
| *Beauveria bassiana* 15CT44 | Apr. 12, 2018 | 67610 |
| *Beauveria bassiana* 16WS07 | Apr. 12, 2018 | 67611 |
| *Metarhizium anisopliae* 16WS10 | Apr. 12, 2018 | 67612 |

All restriction on the availability to the public of these biological materials identified herein and deposited as described herein will be irrevocably removed upon the granting of a patent.

The biological materials identified herein have been deposited under conditions such that access to the microorganisms are available during the pendency of the patent application to one determined by the Commissioner to be entitled thereto under 37 C.F.R. § 1.14 and 35 U.S.C § 122.

The deposited biological materials will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

DETAILED DESCRIPTION OF THE INVENTION

The present invention relates to one or more endophytic fungi, in particular *Beauveria pseudobassiana* strains CT01 (NRRL Access. No. 67405) and CT10 (NRRL Access. No. 67401); *B. amorpha* strain CT14 (NRRL Access. No. 67402); *Metarhizium pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and *M. anisopliae* strain 16WS10 (NRRL Access. No. 67612) in compositions, and methods of use for insect control. In particular, these endophytic fungi strains are biopesticides in that they kill wheat stem sawfly larvae that live inside wheat, barley, triticale and spelt, and Hessian fly larvae that live inside wheat, rye, and barley.

To be clear, because of the life cycle of the plants and the cryptic nature of the wheat stem sawfly and Hessian fly, the biocontrol composition (and more particularly, the fungi described herein) is applied to the outside of a plant or plant seed or to the ground. Then the fungi penetrate into and grow within the plant as an endophytic symbiont. As discussed supra, the larvae of the wheat stem sawfly and Hessian fly live cryptically inside the stem of the grain crop. Thus, to kill the larvae, the fungi must grow inside the plant and be in contact with the larvae inside the plant in order to infect the larvae and kill the larvae. Because these fungi are endophytes, this occurs. It is believed that the fungi do not infect the larvae outside of the plant because the insects are completely enclosed within the plant and thus protected from contact with infectious fungus propagules (conidia) in the environment on the plant's exterior, or applied in a traditional manner to control external foliage feeding insects.

One embodiment of this invention involves one or more biocontrol compositions which contain one or more of these fungal strains (and more particularly, spores or vegetative mycelium) and at least one agriculturally acceptable carrier. The biocontrol compositions are useful to protect these grain crops from wheat stem sawfly larvae and/or Hessian fly larvae and are useful for killing diapausing wheat stem sawfly larvae and/or Hessian fly larvae. Another aspect of this invention involves methods of using these biocontrol compositions to protect wheat, triticale, spelt, rye, and barley from these agricultural pests. Another aspect of this invention involves methods of killing these agricultural pests by applying these biocontrol compositions to (i) soil in which these grain crops currently grow or will grow, (ii) grain crop seeds, (iii) whole plants and/or (iv) parts of the plants.

In addition, the present application relates to methods for protecting wheat, triticale, spelt, rye, and/or barley by inoculating the grain crop plant or parts thereof (e.g., leaf, seed, stems, branches, and roots) with one or more of *B. pseudobassiana* strains CT01 (NRRL Access. No. 67405) and CT10 (NRRL Access. No. 67401); *B. amorpha* strain CT14 (NRRL Access. No. 67402); *M. pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and/or *M. anisopliae* strain 16WS10 (NRRL Access. No. 67612); or a composition containing one or more of these fungi; or by applying to soil one or more of *B. pseudobassiana* strains CT01 (NRRL Access. No. 67405) and CT10 (NRRL Access. No. 67401); *B. amorpha* strain CT14 (NRRL Access. No. 67402); *M. pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and/or *M. anisopliae* strain 16WS10 (NRRL Access. No. 67612); or a biocontrol composition containing one or more of these fungi; or by spraying or coating wheat, triticale, spelt, rye, and/or barley or parts thereof (e.g., leaf, seed, stems, branches, and roots) with one or more of *B. pseudobassiana* strains CT01 (NRRL Access. No. 67405) and CT10 (NRRL Access. No. 67401); *B. amorpha* strain CT14 (NRRL Access. No. 67402); *M. pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and/or *M. anisopliae* strain 16WS10 (NRRL Access. No. 67612); or a biocontrol composition containing one or more of these fungi. One would apply an effective amount of one or more of *B. pseudobassiana* strains CT01 (NRRL Access. No. 67405) and CT10 (NRRL Access. No. 67401); *B. amorpha* strain CT14 (NRRL Access. No. 67402); *M. pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and/or *M. anisopliae* strain 16WS10 (NRRL Access. No. 67612); or biocontrol compositions containing one or more of these fungi in order to kill diapausing wheat stem sawfly larvae and/or active or diapausing Hessian fly larvae.

Described herein are methods of killing insects (wheat stem sawfly larvae and Hessian fly larvae), involving exposing (or treating) the insect larvae to the biocontrol compositions described herein by applying the biocontrol composition to an object (e.g., wheat, triticale, spelt, rye, and/or barley plants and/or parts thereof, seeds of these grain crops) or an area (e.g., soil, water that is to be applied to the soil or onto plants) in need of such treatment. The amount of the biocontrol composition to be applied should be sufficient to kill the insect larvae (an effective amount). Also described herein are methods of reducing insect populations by applying an effective amount of the biocontrol composition to an object or area.

Application of one or more of the *B. pseudobassiana* strains, the *B. amorpha* strain, one or more of the *B. bassiana* strains, the *M. anisopliae* strain, and/or *M. pemphigi* strains or a biocontrol composition containing at least one of these fungi can be performed in a variety of methods, including, but not limited to, foliar sprays, stem injections, soil drenches, immersion, root dipping, or seed coating or encapsulation using known techniques. Further, one can combine other insecticides or pesticides with the biocontrol compositions containing these fungi.

A "spore" is a generic term that includes both "aerial conidia" (also called "conidia") and "blastospores". A conidium is a type of spore that is generated when the fungus is grown on agar or another solid substrate. A blastospore is a type of spore that is generated when the fungus is grown in a liquid fermentation or in an insect.

The terms "object" or "area" as used herein include any place where the presence of the target insect pests (wheat stem sawfly larvae and Hessian fly larvae) are not desirable, such as a field containing wheat, triticale, spelt, rye, and/or barley plants or a field where one intends to plant wheat, triticale, spelt, rye, and/or barley. Thus, the methods include dispensing the fungi (spores or vegetative mycelium), culture in which the fungi were grown (containing spores or vegetative mycelium), or biocontrol compositions described herein into the area via sprays, emulsions, freeze-dried blocks, coatings or vapor form (e.g., an aerosol). One may use devices that allow a slow sustained release of the fungi (spores or vegetative mycelium), culture in which the fungi were grown (containing spores or vegetative mycelium), and/or biocontrol composition into the environment from a sealed canister or chemical or physical (e.g., fabric) matrix. The biocontrol composition can be placed in an area or on an object where the insect pests are not wanted and in a manner that the larvae of the insect pests will contact the biocontrol composition (and more particularly, the fungi) in the plant's stem. Similarly, the biocontrol composition can contain a formulation of fungal spores and/or vegetative mycelium and administered onto the plants or parts thereof, onto the plant's seeds, or onto the soil in a manner such that the larvae of the insect pests will come into contact with the biocontrol composition (and more particularly, the fungi) in the plant's stem.

These fungi can become endophytic within the grain crop plants by application of spores (more specifically, conidia and/or blastospores) to the plant canopy in an aqueous suspension or in an oil-water emulsion or neat-oil spray to the plant canopy. The conidia or blastospores can also be applied as a seed coat, by immersing seed in an aqueous suspension, oil solution, or oil-in-water emulsion or solution of conidia or blastospores, then planting the seeds. Alternatively, one can adhere the spores to seeds using a polymer or wax. Similarly, seedling plant root systems can be immersed in an aqueous suspension, oil solution, or oil-in-water emulsion or solution of spores then transplanted. Endophytism can also be achieved by planting seedlings into soil or potting mix that had been previously mixed with dry conidia, or with conidia, blastospore or young vegetative mycelium (hyphae) suspensions, emulsions, or solutions (aqueous, oil, or oil and water), or by treating the soil around established plants with a soil drench of conidia, blastospores, or vegetative mycelium (hyphae). Also, one can immerse roots into a liquid containing the spores (oil, water, oil and water). The *Metarhizium* and *Beauveria* fungi can also be established as endophytes by being planted into soil that had been treated by incorporation of microsclerotia produced by methods set forth in U.S. Pub. App. US 2016/0000092 entitled "Composition of Entomopathogenic Fungus and Method of Production and Application for Insect Control" and related patent applications, contents of which are expressly incorporated herein. Also, the fungi of this invention could be established as endophytes by producing vegetative mycelium and then applying between approximately $10^4$ to approximately $10^{11}$ CFU of the vegetative mycelium to the seeds of the grain crop (wheat, triticale, spelt, rye, and/or barley) prior to planting the seeds, or as a soil drench to the base of emerging plants.

*B. pseudobassiana* strains CT01 (NRRL Access. No. 67405) and CT10 (NRRL Access. No. 67401); *B. amorpha* strain CT14 (NRRL Access. No. 67402); *M. pemphigi* strains CT19 (NRRL Access. No. 67403) and WS64 (NRRL Access. No. 67404); *B. bassiana* strains 15CT13 (NRRL Access. No. 67609), 15CT44 (NRRL Access. No. 67610), and 16WS07 (NRRL Access. No. 67611); and/or *M. anisopliae* strain 16WS10 (NRRL Access. No. 67612), alone or in combination with at least one other, are effective in killing wheat stem sawfly larvae and Hessian fly larvae because of the endophytic colonization of the grain crop plants by the fungi. This endophytic colonization of the grain crop plant provides a more stable and sustained protection against the insect pests than occurs with normal foliar application of fungi that does not result in endophytic establishment in the grain crop. Without wishing to be bound to any particular hypothesis, the endophytic colonization is more resistant against environmental factors like UV-light, and is resistant against removal by rain. In contrast, other biopesticides, including fungus spores applied in a traditional manner to control insect pests on the surface of the plant, are present only on the surface of wheat (or other grain crops) and are unable to reach the diapausing larvae. Moreover, the endophytic property of the fungi enables the fungi to grow with the plant from seed, to seedling, to mature plant. Thus, treatment of seed is sufficient to impart a substantially life-long protection to the plant.

In one embodiment, the biocontrol composition described herein also contains another insecticide effective for controlling wheat stem sawfly larvae and Hessian fly larvae or larvae of other insect species that diapause in wheat stems. As used herein, the term "insecticide" refers to a material or mixture of materials which induce mortality, disrupt or impede growth, interfere with metamorphosis or other morphogenic functions, cause sterilization, or interfere with feeding, metabolism, respiration, locomotion or reproduction of the targeted insects, or otherwise stress insects making them more susceptible to infection by the fungi. Suitable insecticides include but are not limited to biological controls such as insect growth regulators, and materials that are toxic to insects (i.e., toxicants) such as chemical insecticides, natural products (e.g., botanical extracts such as neem oil), pathogenic nematodes, other fungi, protozoans, or bacteria. In one embodiment, insecticides are slow-acting (i.e., acting over a course of hours, days, weeks, or preferably months) to reduce "avoidance" effects before individuals have distributed the insecticide to other members of the population or colony. Slow-acting insecticides are known in the art. The composition may also contain biological control compositions such as toxins derived from bacteria, fungi, or other organism.

Natural levels of closely related fungi, *Beauveria bassiana* sensu lato and *Metarhizium* anisopliae s.l., range from a few dozen to a few hundred CFUs/g soil with upper natural background levels of approximately 1000 CFU/g soil (Scheepmaker and Butt, Biocontrol Sci. Tech., 20:503-552 (2010)). In contrast, *B. pseudobassiana* strain CT10 (NRRL Access. No. 67401), *B. amorpha* strain CT14 (NRRL Access. No. 67402), *B. pseudobassiana* strain CT01 (NRRL Access. No. 67405), *B. bassiana* strain 15CT13 (NRRL Access. No. 67609), *B. bassiana* strain 15CT44 (NRRL Access. No. 67610), *B. bassiana* strain 16WS07 (NRRL Access. No. 67611), and *M. anisopliae* strain 16WS10 (NRRL Access. No. 67612) were directly isolated from sawfly larvae obtained from three sites out of the forty-five sites that were examined. Only one site (out of the forty-five sites examined) contained sawfly larvae infected with either *M. pemphigi* strain CT19 (NRRL Access. No. 67403) or *M. pemphigi* strain WS64 (NRRL Access. No. 67404). Further, several hundred sawfly larvae at each site were sampled for presence of any fungi but only a few larvae at the four sites actually were infected with the fungi.

The term "effective amount" or "effective concentration" as used herein, means the minimum amount of the composition needed to kill the insect larvae in an area or on an object when compared to the same area or object which is untreated. The precise amount needed will, by necessity, vary in accordance with the target insect; particular composition used; the type and size of area or object to be treated; weather or climatic conditions under which it is applied; and the environment in which the area or object is located. The precise amount of the composition can easily be determined by one skilled in the art given the teachings herein.

In one embodiment, an effective amount or effective concentration of one or more of the *B. pseudobassiana* strains, and/or *B. amorpha* strain, and/or *B. bassiana* strains, and/or *M. pemphigi* strains, and/or *M. anisopliae* strain of this invention or of a biocontrol composition containing at least one of these fungi is from approximately $10^4$ to approximately $10^{12}$ spores (conidia or blastospores) per dose unit. In another embodiment, the concentration of each *B. pseudobassiana* strains, and/or *B. amorpha* strain, and/or *B. bassiana* strains, and/or *M. pemphigi* strains, and/or *M. anisopliae* strain or of the biocontrol composition containing at least one of these fungi can range from approximately $10^5$ to approximately $10^{10}$ spores (conidia or blastospores) per dose unit. In another embodiment, the concentration of each *B. pseudobassiana* strains, and/or *B. amorpha* strain, and/or *B. bassiana* strains, and/or *M. pemphigi* strains, and/or *M. anisopliae* strain or of the biocontrol composition containing at least one of these fungi can range from approximately $10^6$ to approximately $10^9$ spores (conidia or blastospores) per dose unit. In yet another embodiment, the concentration of each *B. pseudobassiana* strains, and/or *B. amorpha* strain, and/or *B. bassiana* strains, and/or *M. pemphigi* strains, and/or *M. anisopliae* strain or of the biocontrol composition containing at least one of these fungi can range from approximately $10^7$ to approximately $10^9$ spores (conidia or blastospores) per dose unit. A "dose unit" can be the measurement of the biocontrol composition which is being distributed/administered/sprayed/etc. Non-limiting examples include a milliliter of a liquid, a gram of a solid, a plant seed, a meter of land, etc.

In another embodiment, one may include two or more different strains of fungi of this invention in the biocontrol composition. Not wishing to be bound to any hypothesis, the fungi of this invention may grow better at different temperatures. For example, one fungal strain may grow better at colder temperatures (e.g., approximately 10° C. to approximately 15° C.) while another fungal strain may grow better at higher temperatures (e.g., approximately 25° C. to approximately 30° C.). Thus, one may want to include fungal strains that thrive at different of temperatures because the temperatures of a grain crop plant can vary widely over the course of the planting and/or growing seasons.

As used herein, the term "agriculturally acceptable carrier" (or "carrier") includes any liquid or solid carrier to which the fungi of the present invention (*B. pseudobassiana* strains CT01 (NRRL Access. No. 67405) and/or CT10 (NRRL Access. No. 67401); and/or *B. amorpha* strain CT14 (NRRL Access. No. 67402); and/or *M. pemphigi* strains CT19 (NRRL Access. No. 67403) and/or WS64 (NRRL Access. No. 67404); and/or *B. bassiana* strains 15CT13 (NRRL Access. No. 67609), and/or 15CT44 (NRRL Access. No. 67610), and/or 16WS07 (NRRL Access. No. 67611); and/or *M. anisopliae* strain 16WS10 (NRRL Access. No. 67612)) can be added and that is not harmful to the fungi of the invention or the plants to which it is being applied. An agriculturally acceptable carrier is any liquid or solid that can be combined with the fungi of this invention and that assists in the application of the fungi of this invention to the soil or seed or plant or parts thereof so that the fungi of this invention grow and colonize the grain crop plants. Non-limiting examples of agriculturally acceptable carriers include talc, starch, sucrose, lactose, and other carbohydrates, polysaccharides, milk/skim milk, cellulose, water, oil, any oil and water emulsion (e.g., an oil-in-water emulsion, an oil-in-water-in-oil emulsion, a water-in-oil emulsion, a water-in-oil-in-water emulsion, an emulsified cream containing oil and water), a buffered solution, aqueous monosorbitan oleate, Polysorbate 80 (polyoxyethylene sorbitan monooleate), Tween 80 (polyethylene glycol sorbitan monooleate), Silwet L-77 (siloxane polyalkyleneoxide copolymer, also known as aqueous polyalkyleneoxide modified heptamethyltrisiloxane, a nonionic organosilicone surfactant co-polymer), other aqueous solutions containing emulsifier(s) and/or surfactant(s), methylcellulose, clay, sand, peat, vermiculite, diatomaceous earth, a cereal grain flour or meal, cotton meal, rice, seeds, plant seeds, and liquid or solid media. The oil may be any paraffinic oil that can be emulsified with water or any vegetable oil that can be emulsified with water. Also, the oil may be more of a solid, e.g., a wax, petroleum jelly, etc. An agriculturally acceptable carrier can also be a polymer, such as polyvinyl alcohol (PVA), polyethylene glycol (PEG), polyacrylic acid (PAA), poly(lactic acid) (PLA), poly(glycolic acid) (PGA), copolymer of poly(lactic-co-glycolic acid) (PLGA), poly($\varepsilon$-caprolactic acid) (PCLA), poly($\beta$-hydroxybutyric acid), poly($\beta$-hydroxyvaleric acid), polydioxanone, poly(ethylene oxide), poly(malic acid), poly(tartronic acid), polyphosphazene, polyethylene (PE), polystyrene (PS), agar (alginate) or other polysaccharides, gelatin, or combinations thereof. In one embodiment, the carrier contains an oil or other lipophilic substance in which the spores (which are lipophilic) can become suspended. The oil or lipophilic substance can attach to plant cuticle (waxy layer) which is lipophilic, thereby assisting in adhering the spores to the plant and generating an environment conducive to fungal germination and penetration of the plant. The carrier should not kill the fungi of the invention. Also, the carrier should release the fungi of the invention into the soil after application to the soil or onto plants after application onto the plants. In one embodiment, the carrier assists in adhering the fungal spores to the plant cuticle so that the spores can germinate and penetrate the plant. In another embodiment, the carrier also creates a favorable environment on the plant to enhance the germination rate of the spores. In one embodiment, such release of the fungi may occur after a period of rain or irrigation or other type of application of water to the soil and/or plant. In another embodiment, the fungi may be released in dry weather. Any carrier that permits the fungi of the present invention to be delivered to the soil and/or target plant in a manner such that the fungi (spores or vegetative mycelium or other part of the fungus) remains viable may be employed in the composition so long as the carrier does not harm native plants and crops. In one embodiment of this invention, the agriculturally acceptable carrier is not the stems of the grain crops in which these insect larvae inhabit. In another embodiment of this invention the agriculturally acceptable carrier is not living or dead wheat stem sawfly larvae, Hessian fly larvae, or larvae of other insect species that diapause in the stems of the grain crops.

Useful surfactants are emulsifiers and/or foam formers, dispersants or wetting agents having ionic or nonionic properties, or mixtures of these surfactants. Non-limiting examples include salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose.

A dry formulation of the fungal spores of the present invention can be produced using methods familiar to those practiced in the art. See, e.g., Jaronski and Jackson, *Mass production of entomopathogenic Hypocreales*, in *Manual of Techniques in Invertebrate Pathology*, 2nd ed., (Lacey L. A., Ed.) New York: Elsevier/Academic Press, pp. 255-284. Many of the carriers described supra can be used to make a dry composition containing the fungal spores. Non-limiting examples include skim milk, sucrose, lactose, dextran, talc, a polymer, and/or wax can be added to the fungal spores to act as both protectants and carrier. In an alternative embodiment, one can freeze-dry a mixture of a polymer and the culture containing fungal conidia or blastospores at the concentrations described above, or a combination of conidia or blastospores from different strains of the fungi of this invention at the concentrations described above. Then one can mix the polymer containing the fungal conidia or blastospores with grain crop seeds or seeds from another desired plant. The polymer/fungus combination sticks to the seeds. Then one can plant the fungi-coated seeds. Another embodiment of this invention involves mixing the fungal conidia or blastospores with finely pulverized carnauba wax to electrostatically bind the conidia or blastospores to the seeds and then combining the mixture with seeds of grain crop plants.

In one embodiment, the biocontrol composition (fungal spores and agriculturally acceptable carrier or vegetative mycelium and carrier) can be in the form of a solution, spore suspension, dispersion, microsclerotia (see U.S. Pub. App. US 2016/0000092 entitled "Composition of Entomopathogenic Fungus and Method of Production and Application for Insect Control" and related patent applications), gel, layer, cream, dip, coating, encapsulation, granule, and the like.

In one embodiment, one or more of the fungi of the present invention (*B. pseudobassiana* strains CT01 (NRRL Access. No. 67405) and/or CT10 (NRRL Access. No. 67401); and/or *B. amorpha* strain CT14 (NRRL Access. No. 67402); and/or *M. pemphigi* strains CT19 (NRRL Access. No. 67403) and/or WS64 (NRRL Access. No. 67404); and/or *B. bassiana* strains 15CT13 (NRRL Access. No. 67609), and/or 15CT44 (NRRL Access. No. 67610), and/or 16WS07 (NRRL Access. No. 67611); and/or *M. anisopliae* strain 16WS10 (NRRL Access. No. 67612)) can be combined with a cereal grain flour or meal and formed into pellets. For example, liquid culture containing approximately $10^8$ to approximately $10^{11}$ blastospores or conidia per Liter of one or more strains of the fungi is freeze-dried using known-in-the-art methods. The freeze-dried culture is then mixed with a cereal grain flour and water and passed through an extruder so that spherical pellets or cylindrical pellets are made, and allowed to dry. One can then spread the pellets onto the soil and/or plants in the area to be treated when the ground is moist, or prior to rain being expected to occur, or prior to irrigating the area. When wet, the cereal grain flour pellets decay and provide food for the fungi. In an alternative embodiment, if one intends to use two or more strains of the fungi, then liquid culture containing approximately $10^7$ to approximately $10^{10}$ blastospores or conidia of each fungal strains are sprayed-dried, and then are mixed with the cereal grain flour and water, are extruded into the desired shape, and are dried. Optional pellet shapes can include, but are not limited to conical, cube, cuboid, prism (hexagonal or other shape), tetrahedron, octahedron, and dodecahedron. The pellets can range in size from approximately 1 mm$^3$ to approximately 10 cm$^3$; or from approximately 10 mm$^3$ to approximately 5 cm$^3$, or from approximately 20 mm$^3$ to approximately 1 cm$^3$. Depending on the pellet's shape and the mode of spreading, one may want to smooth the pellet's edges to improve the spreading of the pellets. One can broadcast spread pellets or aerial spray pellets. One can also plant the pellets.

One can spray the fungal conidia and/or blastospores and/or the biocontrol composition containing the fungal conidia and/or blastospores onto the soil or onto wheat plants. In one embodiment, spraying is performed after a rain or irrigation (when the soil is moist). In another embodiment, spraying is performed shortly before rain is anticipated and/or during periods of high rain probability, and/or prior to irrigating the area of application. In a third embodiment, one sprays during a period of dry weather, when no rain is anticipated, to prevent the fungal conidia and/or blastospores from washing off the plants prior to germination. Application of the fungal spores in liquid or suspension form and/or the biocontrol composition compositions of this invention may be accomplished by ground or aerial spraying using equipment routine to one of skill in the art. The nozzle of the sprayer may be adjusted for size by one of ordinary skill in the art to accommodate the size of the area being treated and any plants in that area, as well as the type and size of presently disclosed carriers.

As discussed supra, one can apply the fungal conidia and/or blastospores of this invention or compositions of this invention onto seed as a seed coating and then drill (plant) the coated seed into the soil or broadcast the coated seed. In one embodiment, the seed coated with the fungal conidia and/or blastospores of this invention or compositions of this invention can be drilled (planted) or broadcast in the fall of the year during a period of high moisture, and the desired seed will spread the fungal conidia and/or blastospores throughout the soil. In another embodiment, the fungal conidia and/or blastospores coated seed can be drilled (planted) or broadcast at any time prior to rain or application of water (irrigate) to the area where the coated seed are drilled (planted) or broadcasted. For example, to make a biocontrol composition containing a seed coated with one or more of the fungal spores described herein, one cultures and processes one or more of the species of fungi to approximately $10^7$ to $10^8$ spores/mL of liquid, and then one can apply the fungal spores to the seed by making a slurry of approximately 10 oz. culture per approximately 60 pounds seed and rotate the slurry in a drum. After the seeds are dry, one can direct drill (planted) or broadcast the biocontrol composition (fungi-coated seed) at recommended seeding rates, which for wheat seed is approximately 60 pounds per acre. Alternatively, one can mix the spores with a wax or polymer and then coat the seeds with wax or polymer containing the spores. If one has freeze-dried culture containing approximately $10^8$ spores/g, then one can apply the fungal spores to the seed by making a slurry of approximately 2 g freeze-dried fungal spores with approximately 60 pounds per acre of seed and rotate the slurry in a drum. After the seeds are dry, one can direct drill (planted) or broadcast seed at recommended seeding rates, which for wheat seed is approximately 60 pounds per acre. For liquid spraying, one can use approximately 10 gallons of aqueous spray containing $10^8$ fungal spores per L per acre of land being treated or 2 g of freeze-dried spores per acre. For 20 acres, apply approximately 80 gallons of liquid per acre or approximately 40 g in 50 to 1000 gallons. Final minimum concentration can be approximately 10 million cells per square foot soil surface. The liquid spray can be applied by back pack sprayer, ground sprayer or aerially applied.

One can have a kit containing spores from one or more of the fungi of this invention (*B. pseudobassiana* strains CT01 (NRRL Access. No. 67405) and/or CT10 (NRRL Access. No. 67401); and/or *B. amorpha* strain CT14 (NRRL Access. No. 67402); and/or *M. pemphigi* strains CT19 (NRRL Access. No. 67403) and/or WS64 (NRRL Access. No. 67404); and/or *B. bassiana* strains 15CT13 (NRRL Access. No. 67609), and/or 15CT44 (NRRL Access. No. 67610), and/or 16WS07 (NRRL Access. No. 67611); and/or *M. anisopliae* strain 16WS10 (NRRL Access. No. 67612)) described herein for reducing the population of wheat stem sawfly larvae and Hessian fly in a field of wheat, triticale, spelt, rye, and/or barley. A kit may contain one or more containers, each having one or more spores of the fungal strains described herein, in a liquid or dry formulation, and written instructions for using the kit to apply to a grain crop field to reduce the population of wheat stem sawfly larvae and Hessian fly in a field of wheat, triticale, spelt, rye, and/or barley. Alternatively, the kit may contain a biocontrol composition containing spores or vegetative mycelium of one or more strains of the fungi described herein. The biocontrol composition can be coated seeds or vegetative mycelium of the fungi combined with another agriculturally acceptable carrier (described supra). The kit may optionally contain one or more insecticides and/or fertilizer that can be applied with the fungi or biocontrol composition. As discussed supra, the concentration of each of *B. pseudobassiana* strains CT01 (NRRL Access. No. 67405) and/or CT10 (NRRL Access. No. 67401); and/or *B. amorpha* strain CT14 (NRRL Access. No. 67402); and/or *M. pemphigi* strains CT19 (NRRL Access. No. 67403) and/or WS64 (NRRL Access. No. 67404); and/or *B. bassiana* strains 15CT13 (NRRL Access. No. 67609), and/or 15CT44 (NRRL Access. No. 67610), and/or 16WS07 (NRRL Access. No. 67611); and/or *M. anisopliae* strain 16WS10 (NRRL Access. No. 67612) within the kit can depend on the number of strains of fungi contained within the kit. For example, if only one of strains of fungi described herein is contained within the kit, the concentration of the fungus may be approximately $10^8$ to approximately $10^9$ conidia or blastospore/ml of applied material. Alternatively, if two of strains of the fungi described herein are within the kit, the concentration for each fungal strain may be only approximately $10^7$ to approximately $10^9$ conidia or blastospore per ml of applied material. As the number of strains increase, the concentration of each strain can decrease.

The terms "approximately" and "about" refers to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a fungus" includes both a single fungus and a plurality of fungi.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. In-Vitro Pathogenicity Assay of Five Fungal Strains

Aerial conidia of the wheat-stem sawfly-derived *B. pseudobassiana* strains CT01 (NRRL Access. No. 67405) and CT10 (NRRL Access. No. 67401), *B. amorpha* strain CT14 (NRRL Access. No. 67402), and *M. pemphigi* strains CT19 (NRRL Access. No. 67403) and WS64 (NRRL Access. No. 67404), and the commercial *B. bassiana* strain GHA are produced on half-strength Sabouraud dextrose agar with 0.1% yeast extract. These cultures represent $3^{rd}$ or $4^{th}$ in-vitro passage of each fungus from its isolation from a sawfly larva, thus ensuring no loss of virulence. The conidia are harvested from mature, sporulated plates of fungus by mechanical scraping into 0.1% aqueous mono sorbitan oleate. The suspension is then filtered to remove any mycelium, to create a stock suspension of the conidia. After the conidial concentration in the stock solution is determined by hemocytometer count, a series of serial dilutions with reverse osmosis water is prepared for administration to 55-mm filter paper disks in 60-mm diameter Petri dishes. Conidial viability of all strains is >95% as determined from conidial germination on potato dextrose agar. Aqueous conidial suspensions of the fungi are applied as a fine spray in 0.3 ml water to each disk, to slightly but evenly dampen each disk, to achieve 10, 30, 100, 300 or 1000 conidia mm$^{-2}$ of filter surface. This administration method simulates a larva encountering low number of conidia on the inner surface of the hollow wheat stem where the conidia have been produced by the endophytic fungus growing out of plant tissue, as the larva moves and feeds. Five diapausing larvae are added to each of 3 replicate disks per dose and are incubated at 20° C. for 9 days. On days 5, 7 and 9 the larvae are examined for mortality. Any dead larvae are removed. The surfaces of dead larvae are disinfected by immersion in 1% NaOCl for 30 seconds, rinsed twice in sterile water, and then are placed in Petri dishes maintained at 100% RH to allow sporulation, if the larvae had been killed by the fungus. The assay is repeated twice or more. An additional bioassay is conducted as described supra but using *B. pseudobassiana* strains CT01 (NRRL Access. No. 67405) and CT10 (NRRL Access. No. 67401), *B. amorpha* strain CT14 (NRRL Access. No. 67402), and *M. pemphigi* strains CT19 (NRRL Access. No. 67403) and WS64 (NRRL Access. No. 67404), at lower doses of 1, 3, 10, 30, or 100 conidia/mm$^{-2}$ and only 7 days of post-treatment observation. A third set of bioassays are conducted as described supra using *B. bassiana* strains 15CT13 (NRRL Access. No. 67609), 15CT44 (NRRL Access. No. 67610), 16WS07 (NRRL Access. No. 67611), and *M. anisopliae* strain 16WS10 (NRRL Access. No. 67612). See Table 2, infra, for the mortality rate of larval wheat-stem sawflies after being confined for 9 days to filter paper treated with conidial suspensions of *B. pseudobassiana* strains CT01 (NRRL Access. No. 67405), CT10 (NRRL Access. No. 67401), *B. amorpha* CT14 (NRRL Access. No. 67402), or *M. pemphigi* strains CT19 (NRRL Access. No. 67403), WS64 (NRRL Access. No. 67404), or *B. bassiana* GHA. See Table 3, infra, for the mortality rate of larval wheat-stem sawflies after being confined for 7 days to filter paper treated with conidial suspensions of *B. pseudobassiana* strains CT01 (NRRL Access. No. 67405), CT10 (NRRL Access. No. 67401), *B. amorpha* CT14 (NRRL Access. No. 67402), or *M. pemphigi* strains CT19 (NRRL Access. No. 67403), WS64 (NRRL Access. No. 67404). See Table 4, infra, for the mortality rate of larval wheat-stem sawflies after being confined for 7 days to filter paper treated with conidial suspensions of *B. bassiana* strains 15CT13 (NRRL Access. No. 67609), 15CT44 (NRRL Access. No. 67610), 16WS07 (NRRL Access. No. 67611), or *M. anisopliae* strain 16WS10 (NRRL Access. No. 67612). Death from mycosis by the fungus used is verified by its external growth and sporulation on the insect cadaver.

TABLE 2

| Percent WSS Larval Mortality on Day 9 | | | | | | |
|---|---|---|---|---|---|---|
| conidia/mm$^2$ | GHA | CT01 | CT10 | CT14 | WS64 | CT19 |
| 0 | 0% | 7% | 20% | 7% | 13% | 7% |
| 10 | 27% | 67% | 87% | 93% | 100% | 87% |
| 30 | 27% | 87% | 100% | 100% | 100% | 93% |
| 100 | 40% | 80% | 100% | 100% | 100% | 100% |
| 300 | 47% | 100% | 100% | 100% | 100% | 100% |
| 1000 | 100% | 100% | 100% | 100% | 100% | 100% |

TABLE 3

Percent WSS Larval Mortality on Day 7

| conidia/mm$^2$ | CT01 | CT10 | CT14 | WS64 | CT19 |
|---|---|---|---|---|---|
| 0 | 7% | 7% | 7% | 7% | 7% |
| 1 | 27% | 7% | 10% | 0% | 0% |
| 3 | 27% | 80% | 40% | 33% | 33% |
| 10 | 33% | 80% | 87% | 40% | 47% |
| 30 | 27% | 87% | 87% | 100% | 80% |
| 100 | 67% | 93% | 100% | 100% | 100% |

TABLE 4

Percent WSS Larval Mortality on Day 7

| conidia/mm$^2$ | 15CT13 | 15CT44 | 16WS07 | 16WS10 |
|---|---|---|---|---|
| 0 | 6% | 6% | 6% | 6% |
| 1 | 27% | 31% | 27% | 58% |
| 3 | 78% | 75% | 66% | 75% |
| 10 | 93% | 72% | 80% | 100% |
| 30 | 100% | 100% | 100% | 100% |
| 100 | 100% | 100% | 100% | 100% |

All of the fungal strains of this invention are highly pathogenic for wheat stem sawfly larvae, even at a dose of 3 conidia/mm$^2$ surface area (Tables 2, 3, and 4 supra). All cadavers are positive for outgrowth of the fungus to which they had been exposed. Untreated larval controls suffer very low mortality, and cadavers have no fungal outgrowth. In comparison, the commercial B. bassiana GHA strain is far less infective, 3- to 100-fold less infective, for larvae than the other fungi.

Example 2. Endophytic Establishment in Wheat

Aerial conidia of B. pseudobassiana strains CT01 (NRRL Access. No. 67405), CT10 (NRRL Access. No. 67401), B. amorpha CT14 (NRRL Access. No. 67402), and M. pemphigi strains CT19 (NRRL Access. No. 67403) and WS64 (NRRL Access. No. 67404) are produced on half-strength Sabouraud dextrose agar with 0.1% yeast extract. These cultures represented 3$^{rd}$ or 4$^{th}$ in-vitro passage from its passage through a sawfly larva. The conidia are harvested from mature, sporulated plates of fungus by mechanical scraping into 0.1% aqueous polyalkyleneoxide modified heptamethyltrisiloxane wetting agent (Silwet L-77®, Helena Chemicals). The suspension is then filtered to remove any mycelium, to create a stock solution of conidia. Conidial concentrations are determined by hemocytometer count. Conidial viabilities are determined by percent germination on potato dextrose agar after 18 hours at 27° C. Final concentrations of conidial suspensions are adjusted for viability. In all cases, viabilities are in excess of 95%.

Wheat (Triticum aestivum L.) varieties Briggs, Choteau, Corbin, Divide, Faller, Glenn, Jerry, McNeil, Mountrail, Mott, Reeder, and Vida are individually grown in a soil-mix within Ray-Leach Cone-tainers™ (Hummert International, Earth City, Mo.) in the greenhouse until Feekes growth stage 6 (stem elongation).

For foliar treatment, an aqueous spray of foliage with suspension of 1×10$^8$ spores/ml of 0.1% Silwet L77 is prepared. Groups of 9 plants are sprayed with one or another of the fungi. Spray volume is 10 ml, which wetted all leaf surfaces but is short of runoff. As a control for the sprayed plants, additional plants are subjected to 20 minutes immersion of entire plants into a suspension of 1×10$^8$ spores/ml (0.1% Silwet L-77). Sprayed and immersed plants are kept at 100% RH for 48 hr after treatment, then moved to greenhouse where they are reared under 16:8 photoperiod, watered daily and fertilized with 20:20:20 liquid fertilizer weekly. Plants are incubated two weeks or to inflorescence, whichever is sooner.

Additional endophytism attempts are conducted with a commercial strains of B. bassiana (GHA, LAM International), M. brunneum (F52, Novozymes Biologicals), and M. anisopliae ESF1 (Lidochem), and an experimental strain of M. robertsii (DWR2009, ARSEF collection, Ithaca, N.Y.), using two varieties of wheat, Choteau and Mott. Conidia of all four fungi are produced on half-strength Sabouraud dextrose agar with 0.1% yeast extract. The conidia are harvested from mature, sporulated plates of fungus by mechanical scraping into 0.1% aqueous Silwet L-77. For this experiment, plants are totally immersed in conidial suspensions as described above. Eight plants of each wheat variety are treated with each fungus and the experiment is conducted twice.

6-8 plants from each treatment group are processed for determination of endophytism as follows. Plants are cut off just below the lowest node, and leaves cut off. Upper parts of the plants are removed about 1-2 cm above the third node, leaving the first and second internodes intact. These internodes are the primary habitat of the wheat stem sawfly larvae. Stems excised from plants are sequentially treated by immersion for 30 seconds in 0.1% Silwet L-77, 2 minutes in 2% acidified NaOCl (pH 5.5) (to which 0.1 ml liquid detergent is added to each liter); 30 seconds in 70% EtOH; and then 30 seconds in two successive sterile water baths. Internode 1 and 2 are then aseptically dissected from each stem. Each 5-cm length of stem internode is then aseptically rolled on potato dextrose agar as a sterility check, after which each internode is aseptically dissected into sliced 1 cm long pieces, which are then split lengthwise. Split pieces are implanted into a selective medium (oatmeal agar containing 0.62 g dodine (N-Dodecylguanidine acetate) a.i., 150 mg chloramphenicol, 2 mg crystal violet (methyl violet 10B or hexamethyl pararosaniline chloride) L-1). These plates of explants are incubated for 7 days at 25° C., are scored for outgrowth, are incubated another 7-10 days, and finally are rescored. Each of the five fungi possesses an easily recognized distinctive morphology, facilitating determination of presence in explanted tissue.

All sterility check plates are "clean" after 14 days—no fungal outgrowth. None of the control plants show fungal outgrowth. Foliar sprays and whole plant immersions result in variable degree of endophytism. Overall, percent colonization by each fungus strain is in Table 5, infra. Colonization via plant immersion is superior to foliar sprays when the data for all wheat varieties are combined. None of the non-wheat stem sawfly fungi demonstrated outgrowth from the wheat stem pieces with exception of B. bassiana, which grew out from only one stem piece of one plant. The wheat variety showing maximum colonization varies for each fungus, with plant immersion superior to foliar spray in all cases.

TABLE 5

Overall Percent Colonization:

| | | By Spray | | | By Immersion | | |
|---|---|---|---|---|---|---|---|
| Strain | Species | Mean | S.D. | Maximum | Mean | S.D. | Maximum |
| CT01 | B. pseudobassiana | 24% | 23.7% | 67% | 50% | 26.4% | 100% |
| CT10 | B. pseudobassiana | 31% | 25.3% | 83% | 65% | 25.6% | 100% |
| CT14 | B. amorpha | 27% | 27.2% | 75% | 57% | 24.1% | 100% |
| CT19 | M. pemghigi | 17% | 22.4% | 67% | 47% | 25.2% | 83% |
| WS64 | M. pemghigi | 24% | 20.2% | 50% | 65% | 20.7% | 100% |
| GHA | B. bassiana | 0% | | | 1% | 3.4% | 8% |
| F52 | M. brunneum | 0% | | | 0% | | |
| ESC1 | M. anisopliae | 0% | | | 0% | | |
| DWR2009 | M. robertsii | 0% | | | 0% | | |

Figure 2:
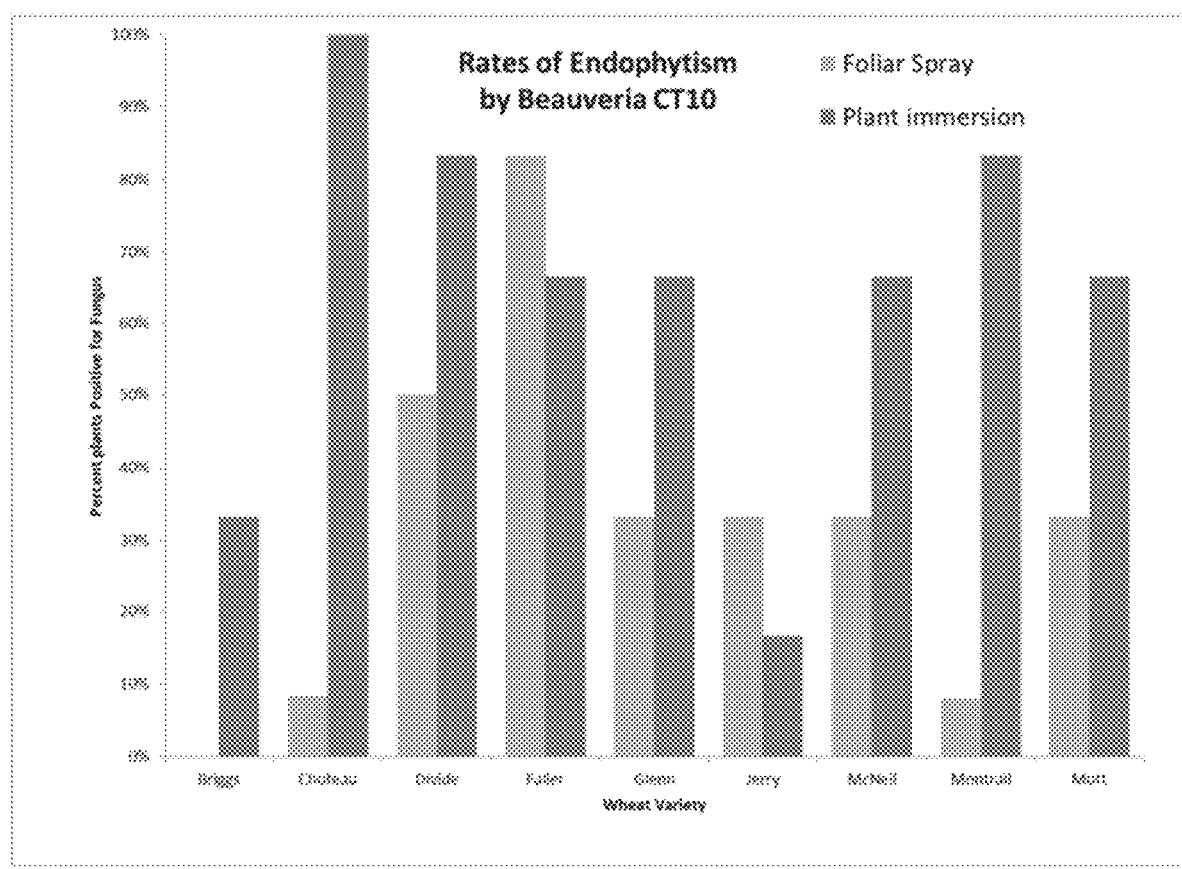
Figure 3:
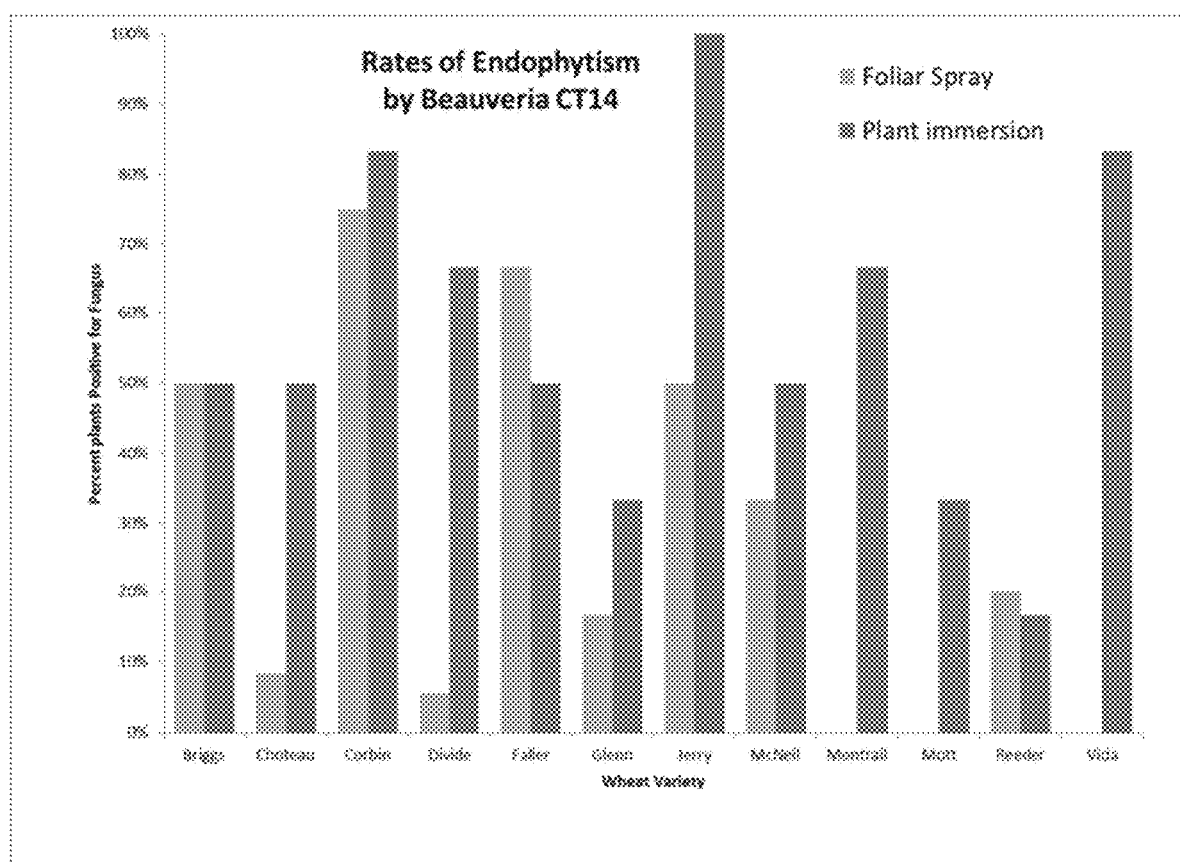
Figure 4:
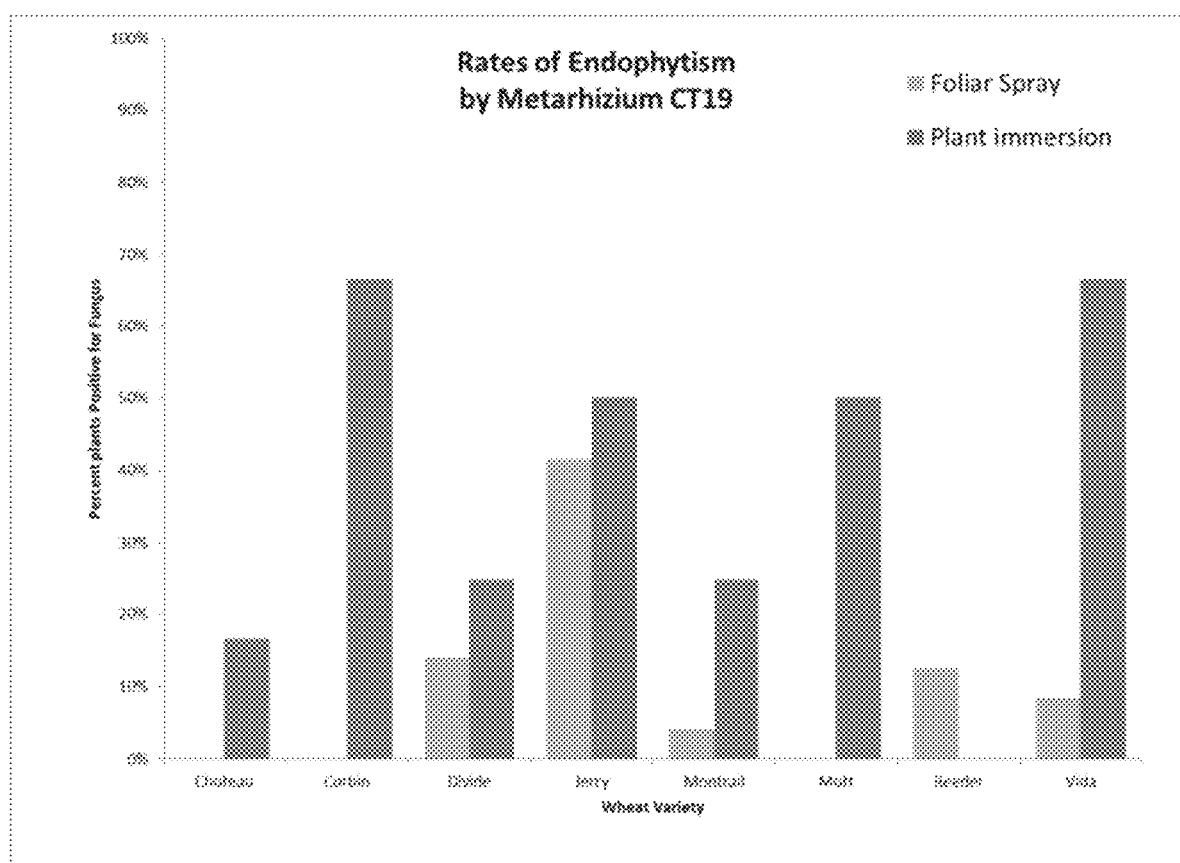
Figure 5:
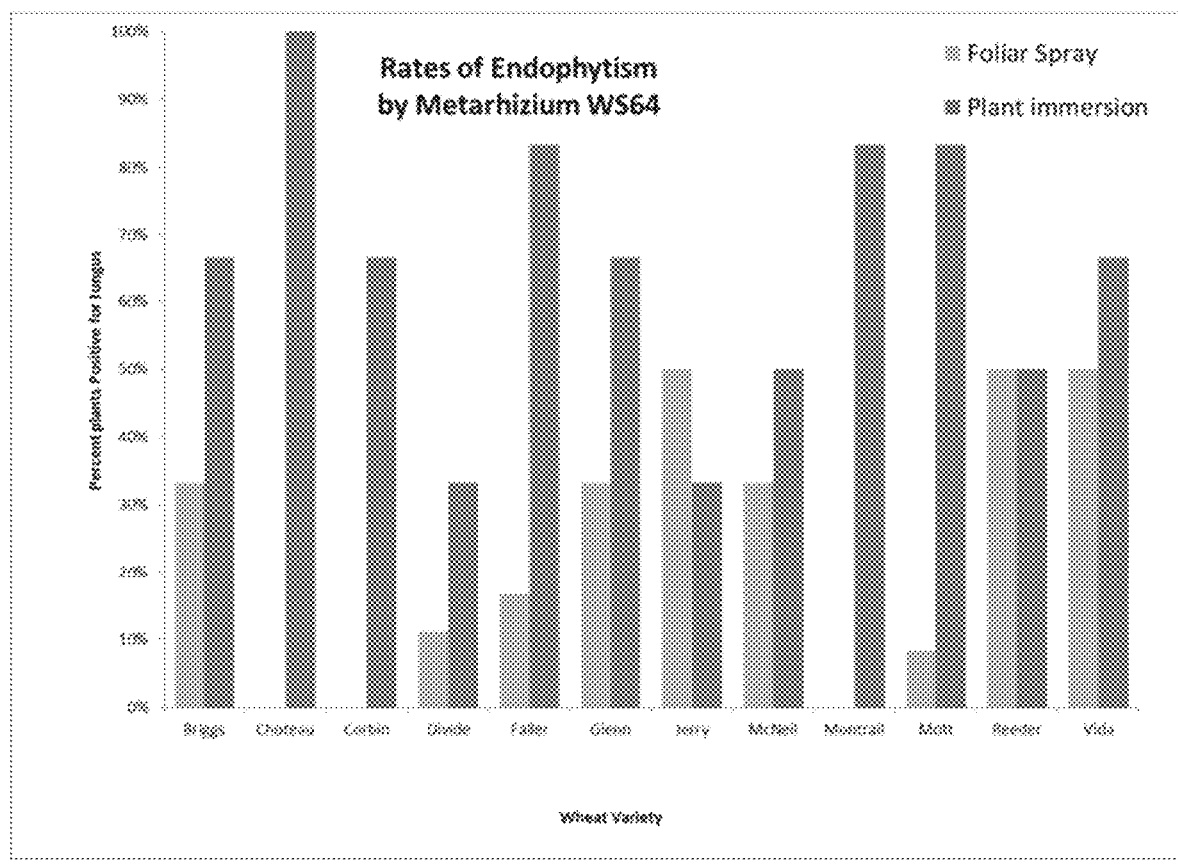
Figure 7:
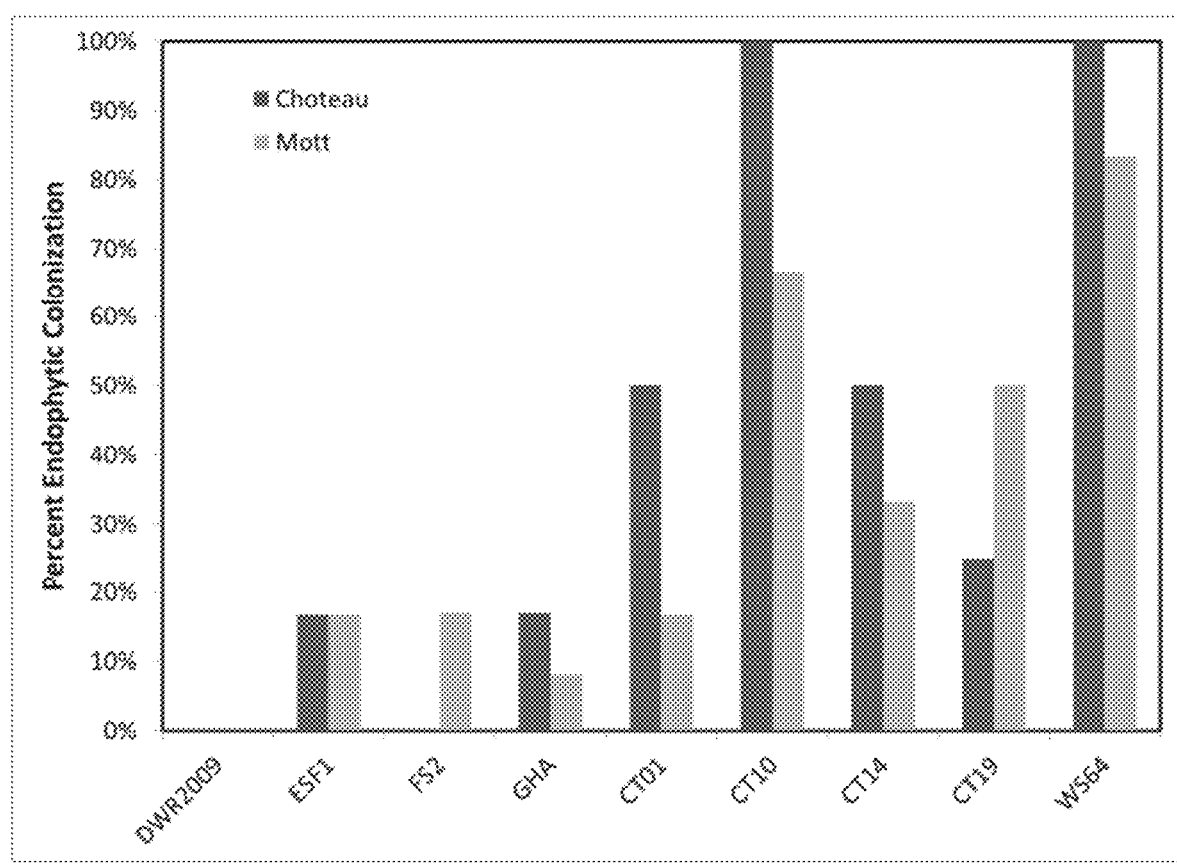

Colonization of each tested wheat variety by each of the indicated fungal strains is presented in FIGS. 1-5. FIG. 1 is the rate of endophytism (percent of treated plants) by *B. pseudobassiana* strain CT01 (NRRL Access. No. 67405) into wheat varieties Briggs, Choteau, Divide, Faller, Glenn, Jerry, McNeil, Mountrail, and Mott. FIG. 2 is the rate of endophytism by *B. pseudobassiana* strain CT10 (NRRL Access. No. 67401) into wheat varieties Briggs, Choteau, Divide, Faller, Glenn, Jerry, McNeil, Mountrail, and Mott. FIG. 3 is the rate of endophytism by *B. amorpha* strain CT14 (NRRL Access. No. 67402) into wheat varieties Briggs, Choteau, Corbin, Divide, Faller, Glenn, Jerry, McNeil, Mountrail, Mott, Reeder, and Vida. FIG. 4 is the rate of endophytism by *M. pemghigi* strain CT19 (NRRL Access. No. 67403) into wheat varieties Briggs, Corbin, Divide, Jerry, Mott, Reeder, and Vida. FIG. 5 is the rate of endophytism by *M. pemghigi* strain WS64 (NRRL Access. No. 67404) into wheat varieties Briggs, Choteau, Corbin, Divide, Faller, Glenn, Jerry, McNeil, Mountrail, Mott, Reeder, and Vida. As evident from FIGS. 1-5 and Table 5, considerable variation in the degree of successful stem colonization exists among the wheat varieties for each of the fungi tested, but plant colonization occurs.

In a similar manner, using the protocols described supra, seedlings of wheat varieties Vida and Reeder are treated individually with *B. bassiana* strains 15CT13 (NRRL Access. No. 67609), 15CT44 (NRRL Access. No. 67610), 16WS07 (NRRL Access. No. 67611), and *M. anisopliae* strain 16WS10 (NRRL Access. No. 67612). Aqueous suspensions of aerial conidia of these four fungi are prepared as described supra to a concentration of $5 \times 10^7$ conidia/ml. Plants grown to stem elongation stage (Feekes' stage 6) are immersed inverted into the conidial suspensions for 20 minutes, then allowed to drain, and then incubated in the greenhouse. After two weeks, at which point the plants are reaching heading stage (Feekes' stage 10), 12 plants from each treatment are processed as described supra with top and next internodes explanted onto the selective agar medium. Colonization (or rate of endophytism) of each tested wheat variety by each of these four fungi is presented in FIG. 6. Extremely high level of endophytism (67-100%) is achieved by these four strains.

Example 3. Use of Oil-in-Water Emulsion Enhances Endophytic Establishment

In an effort to improve endophytic colonization following leaf spray, conidia of *B. pseudobassiana* CT01 (NRRL Access. No. 67405), CT10 (NRRL Access. No. 67401), *B. amorpha* CT14 (NRRL Access. No. 67402), and of *M. pemghigi* CT19 (NRRL Access. No. 67403) and WS64 (NRRL Access. No. 67404), obtained as described supra are suspended in an emulsified solution of water and either paraffinic oil or vegetable oil and sprayed onto groups of 9 wheat plants (varieties Divide and Glenn) at early stem elongation stage. The sprays result in complete coverage but are short of 'run-off.' Alternatively, wheat plants are immersed in either an aqueous or an oil-in-water emulsion suspension of conidia. Control treatments consist of the same conidia suspended in 0.1% Silwet L77 (aqueous spray and aqueous dip in Table 6). Plants are incubated in the greenhouse until boot stage, then are processed as described supra to determine success of endophytism. See Table 6 infra.

TABLE 6

Percent colonization

| Fungus Strain | Aqueous Spray | Oil-Water Emulsion Spray | Plant Immersion in Aqueous Suspension | Plant Immersion in Oil-Water Emulsion |
|---|---|---|---|---|
| WS64 | 17% | 67%* | 33% | 83%* |
| CT19 | 8% | 33%* | 25% | 67%* |
| CT14 | 8% | 33%* | 33% | 83%* |
| CT10 | 25% | 58%* | 42% | 50% |
| CT01 | 17% | 25% | 42% | 83%* |

Asterisk following a percent endophytic establishment indicates significant difference from establishment with the corresponding aqueous application (Chi Square Test, p = 0.05).

Figure 6:
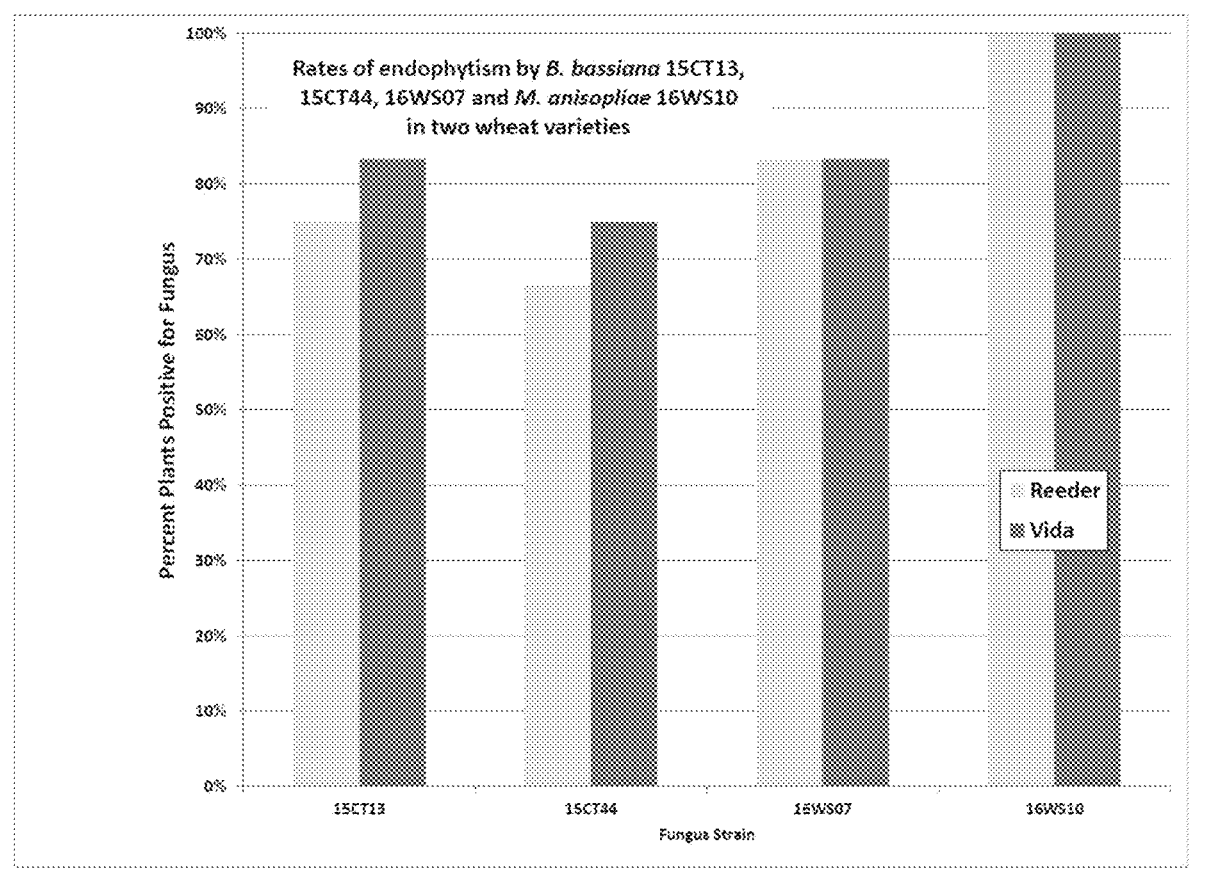

Next, two wheat varieties (Choteau or Mott) at early stem elongation stage undergo foliar application with an oil-in-water emulsion containing $10^8$ conidia obtained using the protocols described supra. The conidia are from commercially available fungi (*M. robertsii* DWR2009, *M. anisopliae* ESF 1, *M. brunneum* F52, and *B. bassiana* GHA) or from fungi of this invention (*B. pseudobassiana* strains CT01 (NRRL Access. No. 67405) and CT10 (NRRL Access. No. 67401), *B. amorpha* strain CT14 (NRRL Access. No. 67402), and *M. pemphigi* strains CT19 (NRRL Access. No. 67403) and WS64 (NRRL Access. No. 67404)). Plants are incubated in the greenhouse until boot stage, then are processed as described supra to determine success of endophytism. FIG. 6 provides the rate of endophytic colonization (as a percentage) for the two varieties of wheat treated with a foliar spray of the oil-in-water emulsion. The Choteau variety wheat has higher rates of endophytic colonization for all of the fungi of this invention compared to the rate for the commercially available fungi, with *B. pseudobassiana* strain CT10 (NRRL Access. No. 67401) and *M. pemphigi* strain WS64 (NRRL Access. No. 67404) having the highest rates. The rate of endophytic colonization of Mott variety wheat with the fungi of this invention is lower than rate of colonization of Choteau variety wheat; only the colonization rate of Mott variety wheat by *B. pseudobassiana* strain CT01 (NRRL Access. No. 67405) is the same as the colonization rate for two of the commercially available fungi.

In additional experiments, dry conidia of *B. pseudobassiana* strain CT10 (NRRL Access. No. 67401) and *M. pemphigi* strain WS64 (NRRL Access. No. 67404) are produced as described supra, and are suspended in an emulsifiable vegetable spray oil (Golden Pest Spray Oil, Stoller Enterprises, Inc., Houston, Tex.) to create an emulsifiable suspension (ES) formulation, simulating a commercial formulation. The ES is mixed with water in three ratios, 1:80 (equivalent to 1 pint ES per 10 gal water), 1:40 (1 quart ES in 10 gal water); and 1:20 (2 quarts ES in 10 gal water). Concentration of conidia in the oils is adjusted so that the final emulsion sprayed consists of $1\times10^8$ conidia/ml spray. These concentrations mimic potential operational application of the fungi to wheat. An additional quantity of conidia of the two fungi are suspended in 0.1% Silwet L77 as a control. Ten ml of each of the preparations are applied to 10-12 wheat seedlings of Vida and Reeder varieties as described supra. Plants are moved to the greenhouse, incubated two weeks, then processed as described supra, to determine extent of endophytism. As shown in Table 7, application of either fungus in 1:40 or greater oil:water emulsion significantly enhances the extent of endophytic colonization by that fungus, compared to a purely aqueous spray.

TABLE 7

| Fungus | Wheat Variety | Treatment | Percent Plants Positive for fungi |
| --- | --- | --- | --- |
| CT10 | Vida | 0.1% Silwet L77 | 38% |
|  |  | 1:80 oil-water emulsion | 50% |
|  |  | 1:40 oil-water emulsion | 75%* |
|  |  | 1:20 oil-water emulsion | 88%* |
| CT10 | Glenn | 0.1% Silwet L77 | 30% |
|  |  | 1:80 oil-water emulsion | 30% |
|  |  | 1:40 oil-water emulsion | 60%* |
|  |  | 1:20 oil-water emulsion | 80%* |
| WS64 | Vida | 0.1% Silwet L77 | 13% |
|  |  | 1:80 oil-water emulsion | 38% |
|  |  | 1:40 oil-water emulsion | 63%* |
|  |  | 1:20 oil-water emulsion | 88%* |
| WS64 | Glenn | 0.1% Silwet L77 | 10% |
|  |  | 1:80 oil-water emulsion | 30% |
|  |  | 1:40 oil-water emulsion | 30% |
|  |  | 1:20 oil-water emulsion | 50%* |

*Denotes datum is significantly different from Silwet control, per Fisher's Test Example 4. Coating Wheat Seed with Fungus Conidia Allows Endophytic Establishment Seeds of wheat, variety Glenn, are immersed in a suspension of $1\times10^8$ conidia of *B. pseudobassiana* strain CT01 (NRRL Access. No. 67405) or strain CT10 (NRRL Access. No. 67401)/ml of 1% methylcellulose, or 0.05% Tween 80 (polyethylene glycol sorbitan monooleate), for two hours, then drained of excess fluid and dried in a laminar air flow hood. After drying, the seeds are planted in vermiculite within Cone-tainers™ (Hummert International, Earth City, Mo.) and grown in the greenhouse to late stem extension (Feekes' Stage 8). At this point, the plants are processed as described supra to determine extent of endophytic establishment. The outcome of this seed treatment results in 83% plants positive for *B. pseudobassiana* strain CT01 (NRRL Access. No. 67405) endophytism and 38% for *B. pseudobassiana* strain CT10 (NRRL Access. No. 67401) when methylcellulose is used. Plants derived from seeds treated with conidia in Tween 80 had 42% endophytism by *B. pseudobassiana* strain CT10 (NRRL Access. No. 67401) and 50% by *B. pseudobassiana* strain CT01 (NRRL Access. No. 67405).

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim as follows:

1. A biocontrol composition comprising an agriculturally acceptable carrier and an effective amount of at least one endophytic fungal strain that kills wheat stem sawfly larvae and Hessian fly larvae, said at least one endophytic fungal strain is selected from the group consisting of *Beauveria pseudobassiana* strain CT01 (NRRL Access. No. 67405), *Beauveria pseudobassiana* strain CT10 (NRRL Access. No. 67401), *Beauveria amorpha* strain CT14 (NRRL Access. No. 67402), *Beauveria bassiana* strain 15CT13 (NRRL Access. No. 67609), *Beauveria bassiana* strain 15CT44 (NRRL Access. No. 67610), *Beauveria bassiana* strain 16WS07 (NRRL Access. No. 67611), *Metarhizium pemphigi* strain CT19 (NRRL Access. No. 67403), *Metarhizium pemphigi* strain WS64 (NRRL Access. No. 67404), and *Metarhizium anisopliae* strain 16WS10 (NRRL Access. No. 67612).

2. The biocontrol composition of claim 1, wherein said effective amount of said endophytic fungal strain is between $10^4$ to $10^{12}$ spores per dose unit.

3. The biocontrol composition of claim 1, wherein said effective amount of said endophytic fungal strain is between $10^4$ to $10^{11}$ CFU vegetative mycelium of said fungal strain per dose unit.

4. The biocontrol composition of claim 1, wherein said agriculturally acceptable carrier is selected from the group consisting of a polymer, a vegetable oil, a vegetable wax, a paraffinic oil, a paraffinic wax, an emulsion of oil and water, an aqueous solution containing a polymer, agar, gelatin, a lipophilic substance that assists the fungi in adhering to the plant or part thereof, and a plant seed.

5. The biocontrol composition of claim 4, wherein said plant seed is a grain crop seed.

6. A kit comprising a first container comprising at least one endophytic fungus that kills wheat stem sawfly larvae or Hessian fly larvae, optionally a second container, and instructions of applying said at least one endophytic fungus to land or a plant; wherein said at least one endophytic fungus is selected from the group consisting of *Beauveria pseudobassiana* strain CT01 (NRRL Access. No. 67405), *Beauveria pseudobassiana* strain CT10 (NRRL Access. No. 67401), *Beauveria amorpha* strain CT14 (NRRL Access. No. 67402), *Beauveria bassiana* strain 15CT13 (NRRL Access. No. 67609), *Beauveria bassiana* strain 15CT44 (NRRL Access. No. 67610), *Beauveria bassiana* strain 16WS07 (NRRL Access. No. 67611), *Metarhizium pemphigi* strain CT19 (NRRL Access. No. 67403), *Metarhizium pemphigi* strain WS64 (NRRL Access. No. 67404), and *Metarhizium anisopliae* strain 16WS10 (NRRL Access. No. 67612).

7. The kit of claim 6, wherein said first container comprises spores or vegetative mycelium of said endophytic fungus.

8. The kit of claim 6, wherein said optional second container comprises an agriculturally acceptable carrier.

9. The kit of claim 8, wherein said agriculturally acceptable carrier is selected from the group consisting of a polymer, a vegetable oil, a vegetable wax, a paraffinic oil, a paraffinic wax, an emulsion of oil and water, an aqueous solution containing a polymer, agar, gelatin, and a lipophilic substance that assists the fungi in adhering to the plant or part thereof.

\* \* \* \* \*